(12) United States Patent
Hitomi et al.

(10) Patent No.: US 9,359,390 B2
(45) Date of Patent: Jun. 7, 2016

(54) ACTIVATED CARBON AND USE THEREFOR

(75) Inventors: Mitsunori Hitomi, Bizen (JP);
Takayuki Yoshikawa, Bizen (JP);
Takayuki Yamada, Bizen (JP)

(73) Assignee: Kuraray Chemical Co., Ltd., Osaka-shi (JP)

( * ) Notice: Subject to any disclaimer, the term of this patent is extended or adjusted under 35 U.S.C. 154(b) by 826 days.

(21) Appl. No.: 13/637,250

(22) PCT Filed: Mar. 24, 2011

(86) PCT No.: PCT/JP2011/057081
§ 371 (c)(1),
(2), (4) Date: Sep. 25, 2012

(87) PCT Pub. No.: WO2011/125504
PCT Pub. Date: Oct. 13, 2011

(65) Prior Publication Data
US 2013/0023405 A1   Jan. 24, 2013

(30) Foreign Application Priority Data
Mar. 31, 2010   (JP) .................. 2010-080010

(51) Int. Cl.
*C07F 9/38* (2006.01)
*B01J 21/18* (2006.01)
*C01B 31/08* (2006.01)
*B01J 35/00* (2006.01)

(52) U.S. Cl.
CPC .............. *C07F 9/3813* (2013.01); *B01J 21/18* (2013.01); *B01J 35/002* (2013.01); *C01B 31/08* (2013.01); *C07F 9/3808* (2013.01)

(58) Field of Classification Search
None
See application file for complete search history.

(56) References Cited

U.S. PATENT DOCUMENTS

| | | | |
|---|---|---|---|
| 4,510,193 A | 4/1985 | Bliicher et al. | |
| 4,624,937 A | 11/1986 | Chou | |
| 2012/0071692 A1* | 3/2012 | Ahrens | B01J 21/066 564/402 |
| 2013/0244862 A1* | 9/2013 | Ivanovici | B01J 21/18 502/101 |

FOREIGN PATENT DOCUMENTS

| | | |
|---|---|---|
| CN | 1183100 A | 5/1998 |
| JP | 60 246328 | 12/1985 |
| JP | 5 811 | 1/1993 |
| JP | 8 81210 | 3/1996 |
| JP | 9 248456 | 9/1997 |
| JP | 2685356 | 12/1997 |
| JP | 3719756 | 11/2005 |
| TW | 204328 B | 4/1993 |
| WO | WO 94/16998 A1 | 8/1994 |

OTHER PUBLICATIONS

Bandosz et al.; Bituminous Coal-Based Activated Carbons Modified with Nitrogen as Adsorbents of Hydrogen Sulfide; Carbon; 42, 469-476; 2004.*
Radovic et al.; On the Modification and Characterization of Chemical Surface Properties of Activated Carbon: In the Search of Carbons with Stable Basic Properties; Langmuir; 12, 4404-4410; 1996.*
Tessmer et al.; Impact of Oxygen Containing Surface Functional Groups on Activated Carbon Adsorption of Phenols; Environ. Sci. Technology; 31,1872-1878, 1997.*
Combined Office Action and Search Report issued Oct. 13, 2014 in Taiwanese Patent Application No. 100110049 (with English language translation).
International Search Report Issued Aug. 16, 2011 in PCT/JP11/57081 Filed Mar. 24, 2011.

* cited by examiner

*Primary Examiner* — Guinever S Gregorio
(74) *Attorney, Agent, or Firm* — Oblon, McClelland, Maier & Neustadt, L.L.P.

(57) ABSTRACT

An activated carbon having a high catalytic activity as an oxidation catalyst or a decomposition catalyst, and use therefor are provided.
The activated carbon has (a) an oxygen content in a range from 1.40 to 4.30% by mass, (b) a nitrogen content in a range from 0.90 to 2.30% by mass, (c) a sulfur content in a range from 0.50 to 1.20% by mass, and (d) a hydrogen content in a range from 0.40 to 0.65% by mass. The activated carbon may have at least one characteristic of (e) an amount of an acidic surface functional group of 0.10 to 0.36 meq/g, (f) an amount of a basic surface functional group of 0.50 to 1.30 meq/g, and (g) a benzene adsorption capacity of 25 to 50%. The activated carbon catalyzes an oxidation reaction of N-(phosphonomethyl)iminodiacetic acid with a peroxide (e.g., hydrogen peroxide) and achieves an efficient production of N-(phosphonomethyl)glycine even after repetitive use. The activated carbon also efficiently decomposes a chloramine.

18 Claims, No Drawings

ACTIVATED CARBON AND USE THEREFOR

TECHNICAL FIELD

The present invention relates to activated carbons useful as a catalyst (e.g., a catalyst for oxidation reaction and a decomposition catalyst) in an organic synthesis or other applications and to applications of the activated carbon using the catalytic activity thereof. More specifically, the present invention relates to, for example, an activated carbon useful as a decomposition catalyst (or an oxidation catalyst) for a peroxide and/or a chloramine (chloroamine) [for example, an activated carbon catalyst which can maintain a decomposing activity for decomposing hydrogen peroxide in an aqueous solution and sustainably maintain the performance in a process for producing N-(phosphonomethyl)glycine from N-(phosphonomethyl)iminodiacetic acid] and to applications of the activated carbon (for example, a process for producing N-(phosphonomethyl)glycine and a process for removing a chloramine).

BACKGROUND ART

Activated carbons are well known to act as catalysts in themselves. For example, activated carbons are known to be useful for various oxidation reactions including oxidation of hydrogen sulfide and that of $SO_2$. It is observed that activated carbons affect such a reaction. Activated carbons as catalysts affect or influence only the rate of the reaction and are hardly changed in themselves by the reaction.

An activated carbon produced from a raw material having a high nitrogen content effectively catalyzes a specific reaction (such as decomposition of hydrogen peroxide) compared with an activated carbon produced from a raw material having a low nitrogen content. Moreover, the activated carbon produced from raw material having a low nitrogen content is also known to increase in a catalytic activity or function thereof when the activated carbon is exposed to a nitrogen-containing compound (such as ammonia) at a high temperature. Nowadays, an activated carbon having a high catalytic activity is produced by carbonizing a material having a high nitrogen content (such as a polyacrylonitrile or a polyamide) at a low temperature or a high temperature and activating the resulting carbonized product. In each case, the activated carbon is produced by heat-treating the raw material at a temperature above 700° C. It is also known that the oxidation of the activated carbon produced from a raw material having a low nitrogen content before or during the exposure to a nitrogen-containing compound is advantageous.

Unfortunately, all of the conventional processes for producing an activated carbon having a catalytic activity have certain disadvantages, thereby limiting an overall usefulness or utility thereof. For example, the raw material having a high nitrogen content (such as a polyacrylonitrile or a polyamide) is expensive and generates a large amount of cyanides and other toxic gas in carbonization. The activated carbon obtained from the raw material having a low nitrogen content requires a violent chemical post-treatment for changing the catalytic capacity significantly. In this regard, a desired catalytic activity is achieved by the sacrifice or reduction of the carbon yield, therefore the resulting activated carbon is inevitably expensive. Further, since the chemical treatment uses a large quantity of a toxic and dangerous chemical (such as nitric acid, sulfuric acid, or ammonia), toxic and dangerous by-products such as SOx, NOx, and a cyanide are produced in significantly large quantities.

Japanese Patent Application Laid-Open Publication No. 60-246328 (JP-60-246328A, Patent Document 1) discloses a process for producing N-(phosphonomethyl)glycine by an oxidation reaction of N-(phosphonomethyl)iminodiacetic acid in the presence of oxygen or an oxygen-containing gas with an activated carbon catalyst in which an oxide has been removed from a surface thereof. This document also discloses that the activated carbon catalyst is obtained by exposing a carbon to an oxidizing agent (e.g., nitric acid) and then pyrolyzing (or thermally decomposing) the carbon in an oxygen-free atmosphere at a temperature of 800 to 1200° C. or by pyrolyzing (or thermally decomposing) a carbon at a temperature of 800 to 1200° C. while passing a gas stream comprising ammonia and an oxygen-containing gas over the carbon. The method for treating the carbon material with the chemical requires use of a toxic and dangerous chemical and produces toxic and dangerous by-products in large quantities, as described above.

There are a large number of conventional arts which deal with the catalytic performance of the activated carbon itself, whereas there are few conventional arts which refer to the relationship between the physical properties of the activated carbon and the catalytic performance thereof in detail except for the following Patent Document 4. The reason includes that the relationship is complicated and difficult to solve due to multiple contributions of various properties of the activated carbon to the catalytic performance.

Japanese Patent No. 2685356 (JP-2685356B, Patent Document. 2) discloses a catalytic-active carbonaceous char for rapidly decomposing hydrogen peroxide in an aqueous solution. This document discloses that the carbonaceous char is produced by oxidation of a bituminous coal or a bituminous coal-like material, in particular, that the carbonaceous char is produced by oxidizing a raw material at a low temperature, exposing the oxidized material to a nitrogen-containing compound (such as urea), heating the resulting material at a high temperature in an inert atmosphere, calcining or activating the resulting material at a high temperature in steam and/or carbon dioxide, and cooling the resulting material in an inert atmosphere. This process is, however, complicated.

Japanese Patent No. 3719756 (JP-3719756B, Patent Document 3) discloses a process for synthesizing a N-(phosphonomethyl)glycine from N-(phosphonomethyl)iminodiacetic acid in coexistence with water, hydrogen peroxide and an activated carbon. This document discloses that a commercially available activated carbon can be used and that the activated carbon is reusable many times. The activated carbon, however, has a low catalytic activity probably due to no optimization of the activated carbon. In addition, recycling of the activated carbon significantly reduces the catalytic activity. Moreover, since this document is silent on an optimizing factor or index of the catalytic activity of the activated carbon, the influence of the activated carbon catalyst relating to the production process of N-(phosphonomethyl)glycine is not revealed.

Japanese Patent Application Laid-Open Publication No. (JP-5-811A, Patent Document 4) disclose an activated carbon as a catalyst for the decomposition of hydrogen peroxide; the activated carbon is made from a protein or a polyacrylonitrile fibrous activated carbon material as a raw material, comprises 1 to 5% by weight of nitrogen, 3 to 30% by weight of oxygen, and 40 to 95% by weight of carbon and has an average pore radius of 15 to 30 Å, and mesopores occupying at least 50% by volume based on the total pore volume. The activated carbon described in Examples of this document comprises 2.1 to 4.1% by weight of nitrogen and 7.6 to 22.8% by weight of oxygen; and that described in Comparative Examples comprises an activated carbon comprising 0.5% by weight of nitrogen and 5.6% by weight of oxygen. These activated carbons, however, not only are insufficient in catalytic activity for decomposing hydrogen peroxide but also sometimes decrease the activity after repetitive use thereof.

Meanwhile, for the disinfection of tap water, a low concentration of a chloramine (chloroamine) is used instead of chlorine. The chloramine includes monochloroamine (monochloramine), dichloroamine, and trichloroamine. Monochloramine is more stable and less vaporizes than chlorine. Moreover, monochloramine does not produce halomethanes even in the presence of methane. Thus use of the chloramine (particularly, monochloramine) is in the process of increasing. In these years, however, many researchers are coming to understand that monochloramine is toxic to an organism, particularly, a freshwater or seawater aquatic organism, and is a causative agent of hemolytic anemia. Accordingly, the development of means for effectively removing the chloramine is required. Moreover, when tap water disinfected with a chloramine is used in an artificial dialyzer, the chloramine permeates through a semipermeable membrane to contact with a blood. Thus, a kidney dialysis unit or other medical units require a high removal of the chloramine.

RELATED ART DOCUMENTS

Patent Documents

Patent Document 1: JP-60-246328A. (Claims, and page 2, the lower left column to the lower right column)
Patent Document 2: JP-2685356B (Claims, and column 4, line 37 to column 5, line 27)
Patent Document 3: JP-3719756B (Claims, and paragraphs [0017] and [0020])
Patent Document 4: JP-5-811A (Claims, Examples, and Comparative Examples)

SUMMARY OF THE INVENTION

Problems to be Solved by the Invention

It is therefore an object of the present invention to provide an activated carbon useful as an oxidation catalyst (or a decomposition catalyst) and applications thereof.

Another object of the present invention is to provide an activated carbon catalyst which maintains a high catalytic activity even after repetitive (or repeated) use and applications thereof.

It is still another object of the present invention to provide an activated carbon catalyst capable of effectively decomposing or removing a peroxide (e.g., hydrogen peroxide) and/or a chloramine (e.g., monochloramine) in an aqueous solution and applications thereof.

It is a further object of the present invention to provide a process for efficiently producing N-(phosphonomethyl)glycine with the catalytic activity of the activated carbon and a process for efficiently decomposing or removing a peroxide (e.g., hydrogen peroxide) and/or a chloramine (e.g., monochloramine).

Means to Solve the Problems

The inventors of the present invention made intensive studies to achieve the above objects and finally found that an activated carbon containing oxygen, nitrogen, sulfur and hydrogen atoms at predetermined concentrations has a significantly improved capability of decomposing hydrogen peroxide, that the activated carbon efficiently catalyzes the oxidation of N-(phosphonomethyl)iminodiacetic acid to produce N-(phosphonomethyl)glycine efficiently, and that the activated carbon effectively oxidative-decomposes a chloramine. The present invention was accomplished based on the above findings.

That is, the activated carbon (active carbon) of the present invention has an oxygen content in a range from 1.40 to 4.30% by mass, a nitrogen content in a range from 0.90 to 2.30% by mass, a sulfur content in a range from 0.50 to 1.20% by mass, and a hydrogen content in a range from 0.40 to 0.65% by mass.

The activated carbon of the present invention is useful as an oxidation catalyst (or a decomposition catalyst), for example, as a catalyst for decomposing a peroxide or a chloramine. The activated carbon (active carbon) catalyst (oxidation catalyst or decomposition catalyst) comprises an activated carbon having an oxygen content of 1.40 to 4.30% by mass (e.g., 1.40 to 3.5% by mass), a nitrogen content of 0.90 to 2.30% by mass (e.g., 0.90 to 2.0% by mass), a sulfur content of 0.50 to 1.20% by mass (e.g., 0.50 to 1.00% by mass), and a hydrogen content of 0.40 to 0.65% by mass (e.g., 0.40 to 0.62% by mass). In the activated carbon catalyst, the oxygen content may be 1.40 to 3.0% by mass, the nitrogen content may be 0.90 to 1.75% by mass, the sulfur content may be 0.50 to 0.90% by mass, and the hydrogen content may be 0.40 to 0.65% by mass.

The peroxide may comprise hydrogen peroxide. The chloramine may comprise monochloroamine.

The activated carbon (an activated carbon catalyst such as an oxidation catalyst or a decomposition catalyst) may further have at least one of the following characteristic selected from the group consisting of (e) an amount of an acidic surface functional group, (f) an amount of a basic surface functional group, and (g) a benzene adsorption capacity:

(e) the amount of the acidic surface functional group is 0.10 to 0.36 meq/g (e.g., 0.10 to 0.30 meq/g), (f) the amount of the basic surface functional group is 0.50 to 1.30 meq/g (e.g., 0.50 to 1.00 meq/g), and (g) the benzene adsorption capacity is 25 to 50% (e.g., 25 to 47%).

The activated carbon of the present invention catalyzes an oxidation of N-(phosphonomethyl)iminodiacetic acid in the presence of a peroxide. Accordingly, the present invention also includes a process for producing N-(phosphonomethyl) glycine, which comprises oxidizing N-(phosphonomethyl) iminodiacetic acid with an oxidizing agent in the presence of an activated carbon; the activated carbon has an oxygen content of 1.40 to 4.30% by mass, a nitrogen content of 0.90 to 2.30% by mass, a sulfur content of 0.50 to 1.20% by mass, and a hydrogen content of 0.40 to 0.65% by mass; and the oxidizing agent comprises a peroxide. In this process, the amount of the activated carbon may be 0.5 to 300 parts by weight or may be 10 to 100 parts by weight relative to 100 parts by weight of N-(phosphonomethyl)iminodiacetic acid. Moreover, the peroxide may be hydrogen peroxide. Further, in the process, the decomposition rate of hydrogen peroxide per gram of the activated carbon per hour may be not less than 1000 mg (that is, the decomposition rate of hydrogen peroxide may be not less than 1,000 mg-$H_2O_2$/g-activated carbon/hr).

The present invention also includes a process for removing a chloramine, which comprises allowing the chloramine to contact with an activated carbon; the activated carbon has an oxygen content of 1.40 to 4.30% by mass, a nitrogen content of 0.90 to 2.30% by mass, a sulfur content of 0.50 to 1.20% by mass, and a hydrogen content of 0.40 to 0.65% by mass. This process achieves efficient removal of the chloramine by decomposing the chloramine effectively to liberate the chlorine.

The characteristics of the activated carbon, i.e., the oxygen content, the nitrogen content, the sulfur content, the hydrogen content, the amount of the acidic surface functional group, the amount of the basic surface functional group, and the benzene adsorption capacity can be measured according to methods described in Examples. The decomposition rate of hydrogen peroxide can also be measured according to a method described in Examples.

Effects of the Invention

The activated carbon of the present invention has a high catalytic activity as an oxidation catalyst or a decomposition catalyst. Moreover, the activated carbon catalyst maintains a high catalytic activity even after repetitive use. Thus, the activated carbon catalyst can effectively decompose a peroxide (e.g., hydrogen peroxide) in an aqueous solution. Further, the activated carbon of the present invention catalyzes an oxidation reaction, and thus the catalytic activity of the activated carbon efficiently produces N-(phosphonomethyl)glycine from N-(phosphonomethyl)iminodiacetic acid in the presence of a peroxide (e.g., hydrogen peroxide). Furthermore, the activated carbon of the present invention is, for example, suitable to decompose a chloramine (e.g., monochloramine) for liberating and removing chlorine. Moreover, compared with an activated carbon produced by the conventional means, the activated carbon of the present invention is markedly useful as a catalyst not only for the decomposition and removal of a peroxide or for the removal of a chloramine but also for a variety of oxidation reactions, e.g., the oxidation of a sulfide (e.g., hydrogen sulfide), the oxidation of sulfur dioxide $SO_2$, and the oxidation of a nitrogen oxide.

DESCRIPTION OF EMBODIMENTS

The activated carbon of the present invention has the following characteristics:

(a) the oxygen content is in the range from 1.40 to 4.30% by mass, (b) the nitrogen content is in the range from 0.90 to 2.30% by mass, (c) the sulfur content is in the range from 0.50 to 1.20% by mass, and (d) the hydrogen content is in the range from 0.40 to 0.65% by mass.

(a) The oxygen content of the activated carbon is about 1.40 to 4.30% by mass, preferably about 1.40 to 3.5% by mass (for example, about 1.40 to 3.0% by mass), and more preferably about 1.40 to 2.8% by mass (for example, about 1.40 to 2.75% by mass). An excessively low oxygen content decreases the catalytic activity, and an excessively high oxygen content lowers or reduces the activity after repetitive use.

(b) The nitrogen content of the activated carbon is about 0.90 to 2.30% by mass, preferably about 0.90 to 2.0% by mass (for example, about 0.90 to 1.75% by mass), and more preferably about 0.90 to 1.50% by mass (for example, about 0.90 to 1.25% by mass). When the nitrogen content is excessively low, the activity is lowered after repetitive use. When the nitrogen content is excessively high, the catalytic activity is decreased.

(c) The sulfur content of the activated carbon is about 0.50 to 1.20% by mass, preferably about 0.50 to 1.00% by mass, and more preferably about 0.50 to 0.90% by mass (for example, about 0.50 to 0.85% by mass). An excessively low sulfur content lowers or reduces the activity after repetitive use, and an excessively high sulfur content decreases the catalytic activity.

Further, (d) the hydrogen content of the activated carbon is about 0.40 to 0.65% by mass (for example, about 0.45 to 0.65% by mass), and preferably about 0.40 to 0.62% by mass (for example, about 0.50 to 0.62% by mass) or may be about 0.55 to 0.65% by mass. When the hydrogen content is excessively low, the catalytic activity is decreased. When the hydrogen content is excessively high, the activity is lowered after repetitive use.

With respect to these elements (a) to (d) of the activated carbon, not a single element content but a plurality of element contents seems to be complexly involved in the catalytic activity. Thus, even if one element content is in the above-mentioned range and other elements beyond the above-mentioned content ranges, the activated carbon deteriorates in the catalytic activity.

Moreover, the activated carbon of the present invention preferably has at least one of the following characteristic among (e) an amount of an acidic surface functional group, (f) an amount of a basic surface functional group, and (g) a benzene adsorption capacity described below.

(e) The activated carbon has an amount of an acidic surface functional group in the range from 0.10 to 0.36 meq/g, preferably 0.10 to 0.30 meq/g (for example, 0.11 to 0.27 meq/g), and more preferably 0.12 to 0.25 meq/g. Either excessively small or excessively large amount of the acidic surface functional group lowers the activity of the activated carbon after repetitive use.

(f) The activated carbon has an amount of a basic surface functional group in the range from 0.50 to 1.30 meq/g, preferably 0.50 to 1.00 meq/g (for example, 0.52 to 0.80 meq/g), and more preferably 0.55 to 0.75 meq/g. Either excessively small or excessively large amount of the basic surface functional group lowers the activity of the activated carbon after repetitive use.

(g) The activated carbon has a benzene adsorption capacity in the range from 25 to 50%, preferably 25 to 47%, and more preferably 27 to 45% or may have a benzene adsorption capacity in the range from 30 to 50%. Either excessively low or excessively high benzene adsorption capacity lowers the activity of the activated carbon after repetitive use.

The activated carbon having such a characteristic is useful as a catalyst such as an oxidation catalyst or a decomposition catalyst. For example, the activated carbon catalyst of the present invention is useful for decomposing (or oxidizing) a peroxide, a chloramine, and other substrates. The peroxide may include, for example, hydrogen peroxide, a peracid (e.g., performic acid, peracetic acid, and perbenzoic acid), and a peroxide (e.g., benzoyl peroxide, diacetyl peroxide, lauroyl peroxide, and ethyl methyl ketone peroxide). A representative peroxide includes hydrogen peroxide.

The chloramine (chloroamine) may be monochloroamine $NH_2Cl$, dichloroamine $NHCl_2$, or trichloroamine $NCl_3$. A representative chloramine widely used for the disinfection of tap water includes monochloroamine, which is low volatile and has a high stability. The residual monochloroamine is therefore removed by treatment with sodium thiosulfate or the like. The activated carbon catalyst of the present invention efficiently decomposes the chloramine (e.g., monochloroamine) to liberate chlorine.

The activated carbon catalyst of the present invention is also useful as a catalyst for many reactions in addition to the decomposition of the peroxide and the chloramine as described above, for example, useful as the oxidation or inversion of a sulfide (e.g., hydrogen sulfide), sulfur dioxide $SO_2$, a nitrogen oxide $NO_x$, and other substrates.

The decomposition (or oxidation) of the peroxide, the chloramine and other substrates may be carried out in an organic solvent (for example, a hydrocarbon such as toluene, an alcohol such as ethanol, an ester, a ketone, an ether, and a carboxylic acid) or an aqueous solvent (water or a mixed solvent containing water and a water-soluble organic solvent), and is usually carried out in water. Moreover, the decomposition or oxidation reaction is practically conducted in the presence of an excessive quantity of the solvent. A gaseous substrate [for example, a sulfide (such as hydrogen sulfide), sulfur dioxide $SO_2$, and a nitrogen oxide $NO_x$] may contact with the activated carbon in the form of a gaseous substrate flow optionally together with an air or an oxygen-containing gas. The concentration of the substrate [for example, a peroxide (such as hydrogen peroxide) and a chloramine (such as monochloroamine)] is not particularly limited to a specific one, and, for example, the peroxide (such as hydrogen peroxide) in a reaction system may have a concentration of about 0.1 to 50% by mass, preferably about 0.5 to 30% by mass, and more preferably about 1 to 20% by mass. According to the present invention, since the substrate can effectively be decomposed or oxidized, the activated carbon catalyst of the present invention is useful for removing a minor quantity of the substrate [for example, a peroxide (such as hydrogen peroxide) and a chloramine (such as monochloroamine)]. When a residual minor quantity of the substrate is treated, for example, the concentration of the substrate may be about 0.1 ppb to 1000 ppm.

The amount of the activated carbon catalyst may be about 0.1 to 500 parts by mass, preferably about 1 to 250 parts by mass, and more preferably about 5 to 100 parts by mass (e.g., about 10 to 50 parts by mass) relative to 100 parts by mass of the substrate (e.g., a peroxide and a chloramine).

The decomposition or oxidation reaction may for example be conducted at a temperature of about 10 to 70° C. and preferably about 20 to 50° C. The decomposition or oxidation reaction may for example be conducted in air or under an oxygen-containing atmosphere or may also be conducted under an inert or inactive gas atmosphere.

The activated carbon catalyst of the present invention is also useful as a catalyst for producing N-(phosphonomethyl) glycine by oxidizing N-(phosphonomethyl)iminodiacetic acid with an oxidizing agent. Specifically, the present invention includes a process for producing N-(phosphonomethyl) glycine by oxidizing N-(phosphonomethyl)iminodiacetic acid with an oxidizing agent in the presence of an activated carbon; wherein the activated carbon has an oxygen content ranging from 1.40 to 4.30% by mass, a nitrogen content ranging from 0.90 to 2.30% by mass, a sulfur content ranging from 0.50 to 1.20% by mass, and a hydrogen content ranging from 0.40 to 0.65% by mass, and the oxidizing agent is a peroxide.

As the peroxide, there may be mentioned the same peroxides as described above. These peroxides may be used alone or in combination. Among the peroxides, a water-soluble peroxide, usually, hydrogen peroxide is employed. As the hydrogen peroxide, a commercially available 30 to 60% by mass aqueous solution can be used. If necessary, the solution may be diluted.

The amount of the peroxide (such as hydrogen peroxide) is about 1.5 to 10 mol, preferably about 2 to 5 mol, and more preferably about 2 to 3 mol (for example, about 2 to 2.5 mol) relative to 1 mol of N-(phosphonomethyl)iminodiacetic acid.

The amount of the activated carbon may be selected from the range in which the activated carbon can catalyze the oxidation with the oxidizing agent, for example, from the range of 0.1 to 500 parts by mass relative to 100 parts by mass of N-(phosphonomethyl)iminodiacetic acid. The amount of the activated carbon relative to 100 parts by mass of N-(phosphonomethyl)iminodiacetic acid is usually about 0.5 to 300 parts by mass, preferably about 5 to 200 parts by mass, and more preferably about 10 to 100 parts by mass (for example, about 20 to 80 parts by mass).

The above-mentioned reaction may be carried out in the presence of an organic solvent. The reaction is usually carried out in the presence of an aqueous solvent, particularly, water. The solvent (particularly, water) is not limited to a specific amount as far as a uniform reaction system can be formed. The amount of the solvent may usually be about 1 to 50 parts by mass and preferably about 2 to 25 parts by mass relative to 1 part by mass of N-(phosphonomethyl)iminodiacetic acid.

The reaction may be carried out at a temperature of about 50 to 100° C., preferably about 55 to 90° C., and more preferably about 60 to 80° C. The reaction may be conducted under an applied pressure or ordinary (normal) pressure, usually under an atmospheric pressure. The reaction may be carried out in air or under an oxygen-containing atmosphere or also carried out under an inert or inactive gas atmosphere.

After the completion of the reaction, if necessary, the reaction mixture can be subjected to a conventional separation and purification step (such as concentration, precipitation, solvent extraction, or recrystallization) to give N-(phosphonomethyl)glycine with a high purity and a high yield. For example, according to the present invention, N-(phosphonomethyl)glycine with a purity of not less than 93% can be obtained in a yield of not less than 80%. Practically, N-(phosphonomethyl) glycine is obtained in an crystalline form by precipitation, recrystallization, or other means from the reaction system.

Further, the activated carbon catalyst of the present invention maintains a high catalytic capacity thereof without the deterioration of the catalytic activity even after repetitive use. For example, in the test method described in Examples (Evaluation of hydrogen peroxide decomposition in aqueous solution and Measurement of decomposition rate of hydrogen peroxide), the decomposition rate of hydrogen peroxide per gram of the activated carbon per hour in a batch aqueous solution is not less than 1,000 mg-$H_2O_2$/g-activated carbon/hr (for example, about 2,000 to 100,000 mg-$H_2O_2$/g-activated carbon/hr, preferably about 2,500 to 75,000 mg-$H_2O_2$/g-activated carbon/hr, and more preferably about 3,000 to 50,000 mg-$H_2O_2$/g-activated carbon/hr). Further, even if the activated carbon is used for such a test method (the decomposition test of hydrogen peroxide in a batch aqueous solution) repeatedly not less than 10 times (for example, about 10 to 25 times and preferably about 12 to 30 times), the activated carbon maintains or possesses a high catalytic activity thereof. That is, the activated carbon catalyst of the present invention can be used repeatedly not less than 10 times while maintaining a hydrogen peroxide decomposition efficiency, in an aqueous solution, of not less than 1,000 mg-$H_2O_2$/g-activated carbon/hr in the above-mentioned test method. More specifically, in the method described in Examples (Evaluation of hydrogen peroxide decomposition in aqueous solution and Measurement of decomposition rate of hydrogen peroxide), the coexistence of both hydrogen peroxide and the activated carbon catalyst of the present invention in an N-(phosphonomethyl)iminodiacetic acid aqueous solution can achieve the production of N-(phosphonomethyl)glycine with a purity of not less than 93% in a yield of not less than 80% even if the number of repetitive use is not less than 10.

The activated carbon catalyst is usually produced by oxidizing an activated carbon with nitric acid or sulfuric acid, sodium hypochlorite or other oxidative chemicals and then allowing the oxidized activated carbon to contact with ammonia at a high temperature, or by activating or carbonizing a nitrogen-rich raw material (such as a polyacrylonitrile).

According to the present invention, a variety of activated carbons, each having a high catalytic activity, can be produced at a low cost by the management or control of a plurality of parameters.

Specifically, the activated carbon catalyst of the present invention can be obtained by carbonizing a carbonaceous material and heat-treating the carbonized carbon material under a mixed gas atmosphere containing water vapor, nitrogen and carbon dioxide at a temperature of 850° C. to 1000° C. over 3 to 48 hours. In the heat treatment, the carbonized carbon material may partly be gasified.

The carbonaceous material may be selected from all known materials suitable for producing an activated carbon. For example, the carbonaceous material may include a plant (e.g., a coconut shell, a chaff (a rice hull), a coffee ground, and a wood), a natural polymer (e.g., a starch, a cellulose, and a lignin), a semisynthetic polymer (e.g., a cellulose ester, a cellulose ether, and a lignin resin), a synthetic polymer (e.g., a phenol-series resin, a furan-series resin, and an epoxy resin), and a bituminous material. These raw materials may be used alone or in combination. The raw material may preferably be a plant raw material such as a wood. In particular, a coal containing nitrogen or sulfur (for example, a coal selected from the group consisting of peat, lignite, subbituminous coal, bituminous coal, semianthracitic coal, and anthracite coal) is preferably used.

The activated carbon of the present invention is produced by general activated carbon production facilities, for example, a fluidized bed, a multiple (or multistage) furnace, and a revolving (or rotary) furnace.

The carbonization can be carried out by a conventional method, for example, by heating a carbonaceous material while cutting off oxygen or air at a temperature of 400 to 800° C., preferably 500 to 800° C., and more preferably 600 to 800° C.

The heat treatment (activation) of the carbonized product can be carried out at a temperature above 750° C., preferably 850 to 1000° C. (e.g., 850 to 950° C.) under an atmosphere of a mixture (a mixture atmosphere, a mixed gas) containing water vapor, nitrogen, and carbon dioxide in a fluidized bed, a multiple (or multistage) furnace, or a revolving (or rotary) furnace. The activation under the mixture atmosphere makes the carbonized product gasify partly to provide an activated carbon. The gas (a mixed gas composed of water vapor, nitrogen, and carbon dioxide) for gasifying part of the carbonized product of the carbonaceous material can also be obtained by burning other combustibles containing a natural gas, a petroleum, or a hydrocarbon. The activation temperature usually varies in a range of about ±25° C.

The activation time may be about 3 to 48 hours, preferably about 4 to 24 hours, and more preferably about 5 to 20 hours (for example, about 6 to 12 hours). When the activation time is too short, the activity of the activated carbon is decreased; whereas when the activation time is too long, the productivity is decreased.

The gas partial pressure has a water vapor partial pressure of about 7.5 to 40% and preferably about 10 to 30% (for example, about 10 to 20%), a carbon dioxide partial pressure of about 10 to 50% and preferably about 15 to 45% (for example, about 20 to 40%), and a nitrogen partial pressure of about 30 to 80% and preferably about 40 to 70% (for example, about 45 to 65%). The gas partial pressure may have a water vapor partial pressure of about 10 to 40%, a carbon dioxide partial pressure of about 10 to 40%, and a nitrogen partial pressure of about 40 to 80%. The total pressure of the gas is usually one atmosphere (about 0.1 MPa). An excessively low water vapor partial pressure makes the activation insufficient, whereas an excessively high water vapor partial pressure deteriorates the activity of the activated carbon. When the carbon dioxide partial pressure is excessively low, the activation is insufficient, whereas when the carbon dioxide partial pressure is excessively high, the activity of the activated carbon is deteriorated. An excessively low nitrogen partial pressure deteriorates the activity of the activated carbon, whereas an excessively high nitrogen partial pressure makes the activation insufficient.

Moreover, the total gas supply (flow rate) is about 10 to 50 L/minute, preferably about 15 to 45 L/minute, and more preferably about 20 to 40 L/minute relative to 100 g of the carbonaceous product as a raw material. An excessively low flow rate makes the activation insufficient, whereas an excessively high flow rate deteriorates the activity of the activated carbon.

Combination of such conditions achieves an activated carbon catalyst having objective oxygen content, nitrogen content, sulfur content, and hydrogen content. The details of the process for producing the activated carbon catalyst of the present invention will be referred to Examples.

The activated carbon may be in the form of powder, particle, or granule. If necessary, the activated carbon may be formed into honeycomb or other shapes.

EXAMPLES

The following examples are intended to describe this invention in further detail and should by no means be interpreted as defining the scope of the invention.

The performance of the activated carbons of the following Examples and Comparative Examples were evaluated as follows.

[Evaluation of Hydrogen Peroxide Decomposition in Aqueous Solution and Measurement of Decomposition Rate of Hydrogen Peroxide]

To 400 mL of an aqueous solution having a hydrogen peroxide concentration of 3,000 mg/L at 25° C. was added 0.1 g of a dry activated carbon. The concentration of hydrogen peroxide remaining in the aqueous solution was measured. The change of the hydrogen peroxide concentration with time course was evaluated until the residual hydrogen peroxide reached zero.

$$\text{Decomposition rate of hydrogen peroxide} = (C_0 - C) \times 0.4/A/T$$

$C_0$=Initial concentration (mg/L) of hydrogen peroxide,
$C$=Concentration (mg/L) of hydrogen peroxide after a given time,
$A$=Amount (g) of the activated carbon,
$T$=Given time (hr)

Evaluation of hydrogen peroxide decomposition in repetitive use was performed as follows: a hydrogen peroxide aqueous solution having a concentration of 30% by mass was added to the solution having a residual hydrogen peroxide of zero in order to obtain the hydrogen peroxide concentration of 3000 mg/L, the change of the hydrogen peroxide concentration with time course was evaluated again until the residual hydrogen peroxide reached zero. This procedure was repeated until the decomposition rate of hydrogen peroxide was less than 1,000 mg-$H_2O_2$/g-activated carbon/hr.

[Measurements of Nitrogen, Sulfur, and Hydrogen Contents of Activated Carbon]

The nitrogen, sulfur, and hydrogen contents of the activated carbon were measured by Vario EL III (manufactured by ELEMENTAR) using sulfanilic acid as a reference material. In consideration of scattering of each measured value, an activated carbon P-GLCR (manufactured by Kuraray Chemical Co., Ltd.) as a standard sample was measured in parallel for correcting each measured value, and the nitrogen, sulfur, and hydrogen contents of the activated carbon were determined.

[Measurement of Oxygen Content of Activated Carbon]

The oxygen content of the activated carbon was measured by Vario EL III (manufactured by ELEMENTAR) using benzoic acid as a reference material. In consideration of scattering of each measured value, an activated carbon P-GLCR (manufactured by Kuraray Chemical Co., Ltd.) as a standard sample was measured in parallel for correcting each measured value, and the oxygen content of the activated carbon was determined.

[Measurement of Amount of Acidic Surface Functional Group of Activated Carbon]

An activated carbon (0.5 g) was added to 25 mL of 0.1 mol/L-sodium ethoxide aqueous solution at 25° C., and the mixture was shaken for 24 hours. Thereafter, the mixture was centrifuged by a centrifugal separator to precipitate the activated carbon, and 10 mL of a supernatant was collected and titrated with 0.1 mol/L-HCl to determine an amount of the acidic surface functional group.

[Measurement of Amount of Basic Surface Functional Group of Activated Carbon]

An activated carbon (0.5 g) was added to 25 mL of 0.1 mol/L-HCl aqueous solution at 25° C., and the mixture was shaken for 24 hours. Thereafter, the mixture was centrifuged by a centrifugal separator to precipitate the activated carbon, and 10 mL of a supernatant was collected and titrated with 0.1 mol/L-NaOH to determine an amount of the basic surface functional group.

[Measurement of Benzene Adsorption Capacity of Activated Carbon]

In accordance with the test methods for activated carbon in Japanese Industrial Standards, JIS K1474, the benzene adsorption capacity of the activated carbon was measured.

[Process for Carbonizing and Activating Carbonaceous Raw Material]

In order to determine the effects of various raw materials, activated carbons were produced from different raw materials. Specifically, a carbonaceous raw material was carbonized at 700° C.; 500 g of the resulting carbonized product was then thrown in a furnace; water vapor, carbon dioxide gas, and nitrogen gas, each varying a predetermined partial pressure, were fed into the furnace at 850 to 980° C. at a total gas pressure of one atmosphere and a predetermined flow rate; and the carbonized product was activated for a predetermined activation time to produce an activated carbon.

Process for Producing N-(phosphonomethyl)glycine

To 100 mL of water, 5 g of an activated carbon shown in Table 1 and 20.0 g of N-(phosphonomethyl)iminodiacetic acid were added. Into the mixture, 20.0 g of a hydrogen peroxide aqueous solution having a concentration of 30% by mass was added dropwise over 3 hours at 65° C. under stirring while maintaining the temperature of 65° C. After the completion of the dropping, the resulting mixture was maintained for 1 hour, and N-(phosphonomethyl)glycine was then isolated as a crystal. The isolated crystal was quantitatively determined by a high-speed liquid chromatography, and the weight yield and purity were measured.

Comparative Examples 1 to 7

Each of various raw materials shown in Table was subjected to the above-mentioned carbonization treatment, and the resulting carbonized product was placed in a furnace. A mixed gas having a water vapor partial pressure of 30%, a carbon dioxide partial pressure of 30%, and a nitrogen partial pressure of 40% was introduced into the furnace at a flow rate of 40 L/minute relative to 500 g of the resulting carbonized product, and the carbonized product was treated at an activation temperature of 900° C. for an activation time of one hour to produce an activated carbon.

In the above-mentioned Comparative Examples, the following carbonaceous raw materials were used.

Comparative Example 1: anthracite coal
Comparative Example 2: soft coal
Comparative Example 3: bituminous coal
Comparative Example 4: petroleum coke
Comparative Example 5: insolubilized fibrous polyacrylonitrile (PAN)
Comparative Example 6: coconut shell charcoal
Comparative Example 7: wood charcoal The activated carbon of Comparative Example 1 (raw material: anthracite coal) proved to have the nitrogen content, the sulfur content, and the hydrogen content, each being beyond given ranges, and to have the number of repetitive use as a catalyst being as low as 1.

The activated carbon of Comparative Example 2 (raw material: soft coal) proved to have the nitrogen content and the sulfur content, each being beyond given ranges, and to have the number of repetitive use as a catalyst being as low as 1.

The activated carbon of Comparative Example 3 (raw material: bituminous coal) proved to have the oxygen content, the nitrogen content, and the sulfur content, each being beyond given ranges, and to have the number of repetitive use as a catalyst being as low as 3.

The activated carbon of Comparative Example 4 (raw material: petroleum coke) proved to have the oxygen content, the sulfur content, and the hydrogen content, each being beyond given ranges, and to have the number of repetitive use as a catalyst being as low as 5.

The activated carbon of Comparative Example 5 (raw material: polyacrylonitrile (PAN)) proved to have the nitrogen content and the sulfur content, each being beyond given ranges, and to have the number of repetitive use as a catalyst being 9.

The activated carbon of Comparative Example 6 (raw material: coconut shell charcoal) proved to have the sulfur content and the hydrogen content, each being beyond given ranges, and to have the number of repetitive use as a catalyst being as low as 1.

The activated carbon of Comparative Example 7 (raw material: wood charcoal) proved to have the oxygen content, the nitrogen content, and the hydrogen content, each being beyond given ranges, and to have the number of repetitive use as a catalyst being as low as 3.

Comparative Examples 8 and 9

To 100 g of the activated carbon of Comparative Example 2 was added 1 L of 6-N nitric acid, and the resultant was boiled over 1 hour and then washed with water to produce an activated carbon of Comparative Example 8. The activated carbon of Comparative Example 8 proved to have the oxygen content, the sulfur content, and the hydrogen content, each being beyond given ranges, and to have the number of repetitive use as a catalyst being as low as 1.

The activated carbon of Comparative Example 8 was heat-treated at 930° C. for 3 hours under a nitrogen atmosphere to produce an activated carbon of Comparative Example 9. The activated carbon of Comparative Example 9 proved to have the sulfur content being beyond a given range and to have the number of repetitive use as a catalyst being as low as 4.

Comparative Example 10

To 100 g of the activated carbon of Comparative Example 4 was added 1 L of 6-N nitric acid, and the resultant was boiled over 1 hour and then washed with water to produce an activated carbon of Comparative Example 10. The resulting activated carbon proved to have the oxygen content, the nitrogen content, the sulfur content, and the hydrogen content, each being beyond given ranges, and to have the number of repetitive use as a catalyst being as low as 1.

Comparative Example 11

An activated carbon of Comparative Example 11 was produced in the same manner as in Comparative Examples 1 to 7 except that bituminous coal was used as the carbonaceous raw material and that the activation was conducted at an introduction rate of the mixed gas of 20 L/minute for an activation time of 2 hours. The resulting activated carbon proved to have the oxygen content being beyond a given range and to have the number of repetitive use as a catalyst being 6.

Comparative Example 12

An activated carbon of Comparative Example 12 was produced in the same manner as in Comparative Example 11 except that soft coal was used as the carbonaceous raw material. The resulting activated carbon proved to have the hydrogen content being beyond a given range and to have the number of repetitive use as a catalyst being 3.

Comparative Example 13

As an activated carbon, "KURARAY COAL KW" manufactured by Kuraray Chemical Co., Ltd. (an activated carbon made of bituminous coal as a raw material) described in Patent Document 3 was used. The activated carbon proved to have the oxygen content, the nitrogen content, and the sulfur content, each being beyond given ranges, and to have the number of repetitive use as a catalyst being as low as 3.

Comparative Example 14

As an activated carbon, "KURARAY COAL GC" manufactured by Kuraray Chemical Co., Ltd. (an activated carbon made of coconut shell as a raw material) described in Patent Document 3 was used. The activated carbon proved to have the sulfur content being beyond a given range and to have the number of repetitive use as a catalyst being as low as 1.

Comparative Example 15

As an activated carbon, "KURARAY COAL GLC" manufactured by Kuraray Chemical Co., Ltd. (an activated carbon made of coconut shell as a raw material) described in Patent Document 3 was used. The activated carbon proved to have all of the oxygen content, the nitrogen content, the sulfur content, and the hydrogen content, each being beyond given ranges, and to have the number of repetitive use as a catalyst being as low as 1.

Comparative Example 16

The activated carbon of Comparative Example 5 was heat-treated at 930° C. for 3 hours under a nitrogen atmosphere to produce an activated carbon of Comparative Example 16. The resulting activated carbon proved to have the nitrogen content, the sulfur content, and the hydrogen content, each being beyond given ranges, and to have the number of repetitive use as a catalyst being 9.

Example 1

Bituminous coal as a carbonaceous raw material was subjected to the above-mentioned carbonization treatment, and the resulting carbonized product was placed in a furnace. A mixed gas having a water vapor partial pressure of 20%, a carbon dioxide partial pressure of 40%, and a nitrogen partial pressure of 40% was introduced into the furnace at a flow rate of 10 L/minute relative to 500 g of the resulting carbonized product, and the carbonized product was treated at an activation temperature of 900° C. for an activation time of 5 hours to produce an activated carbon of Example 1. The resulting activated carbon proved to have all values of the physical properties being within given ranges and to have the number of repetitive use as a catalyst being 15.

Example 2

An activated carbon of Example 2 was produced in the same manner as in Example 1 except that anthracite coal was used as the carbonaceous raw material. The resulting activated carbon proved to have all values of the physical properties being within given ranges and to have the number of repetitive use as a catalyst being 14.

Example 3

An activated carbon of Example 3 was produced in the same manner as in Example 1 except that wood charcoal was used as the carbonaceous raw material. The resulting activated carbon proved to have all values of the physical properties being within given ranges and to have the number of repetitive use as a catalyst being 13.

Example 4

Bituminous coal as a carbonaceous material was subjected to the above-mentioned carbonization treatment, and the resulting carbonized product was placed in a furnace. A mixed gas having a water vapor partial pressure of 10%, a carbon dioxide partial pressure of 20%, and a nitrogen partial pressure of 70% was introduced into the furnace at a flow rate of 20 L/minute relative to 500 g of the resulting carbonized product, and the carbonized product was treated at an activation temperature of 900° C. for an activation time of 20 hours to produce an activated carbon of Example 4. The resulting activated carbon proved to have all values of the physical properties being within given ranges and to have the number of repetitive use as a catalyst being 13.

Example 5

Bituminous coal as a carbonaceous material was subjected to the above-mentioned carbonization treatment, and the resulting carbonized product was placed in a furnace. A mixed gas having a water vapor partial pressure of 15%, a carbon dioxide partial pressure of 30%, and a nitrogen partial pressure of 55% was introduced into the furnace at a flow rate of 10 L/minute relative to 500 g of the resulting carbonized product, and the carbonized product was treated at an activation temperature of 900° C. for an activation time of 10 hours to produce an activated carbon of Example 5. The resulting activated carbon proved to have all values of the physical properties being within given ranges and to have the number of repetitive use as a catalyst being 14.

Example 6

Bituminous coal as a carbonaceous material was subjected to the above-mentioned carbonization treatment, and the resulting carbonized product was placed in a furnace. A mixed gas having a water vapor partial pressure of 15%, a carbon dioxide partial pressure of 20%, and a nitrogen partial pressure of 65% was introduced into the furnace at a flow rate of 10 L/minute relative to 500 g of the resulting carbonized product, and the carbonized product was treated at an activation temperature of 900° C. for an activation time of 18 hours to produce an activated carbon of Example 6. The resulting activated carbon proved to have all values of the physical properties being within given ranges and to have the number of repetitive use as a catalyst being 15.

The evaluation results of the activated carbons obtained in Examples 1 to 6 and Comparative Examples 1 to 16 are shown in Table 1.

TABLE 1

| Sample No. | Raw material | Number of repetitions of catalyst (times) | Oxygen content (%) | Nitrogen content (%) | Sulfur content (%) | Hydrogen content (%) | Amount of acidic surface functional group (meq/g) | Amount of basic surface functional group (meq/g) | Benzene adsorption capacity (%) |
|---|---|---|---|---|---|---|---|---|---|
| Com. Ex. 1 | Anthracite coal (activation time: 1 hr) | 1 | 1.93 | 0.25 | 0.22 | 0.95 | 0.100 | 0.944 | 32.4 |
| Com. Ex. 2 | Soft coal (activation time: 1 hr) | 1 | 2.77 | 0.86 | 0.25 | 0.51 | 0.159 | 1.528 | 26.5 |
| Com. Ex. 3 | Bituminous coal (activation time: 1 hr) | 3 | 1.28 | 0.82 | 0.45 | 0.60 | 0.081 | 0.602 | 30.0 |
| Com. Ex. 4 | Petroleum coke (activation time: 1 hr) | 5 | 0.98 | 2.11 | 1.53 | 0.33 | 0.251 | 0.179 | 33.0 |
| Com. Ex. 5 | PAN (activation time: 1 hr) | 9 | 4.07 | 4.72 | 0.27 | 0.53 | 0.297 | 0.175 | 7.6 |
| Com. Ex. 6 | Coconut shell activated carbon (activation time: 1 hr) | 1 | 2.77 | 1.66 | 0.48 | 0.37 | 0.103 | 0.884 | 31.6 |
| Com. Ex. 7 | Wood charcoal (activation time: 1 hr) | 3 | 1.35 | 0.55 | 0.73 | 0.72 | 0.682 | 0.381 | 32.8 |
| Com. Ex. 8 | Com. Ex. 2 treated with 6-N nitric acid | 1 | 5.15 | 1.46 | 0.41 | 0.68 | 0.631 | 0.010 | 29.1 |
| Com. Ex. 9 | Com. Ex. 8 treated at 930° C. | 4 | 3.08 | 1.78 | 0.42 | 0.53 | 0.481 | 0.560 | 33.0 |
| Com. Ex. 10 | Com. Ex. 4 treated with 6-N nitric acid | 1 | 4.35 | 2.35 | 1.23 | 0.87 | 0.566 | 0.783 | 31.0 |
| Com. Ex. 11 | Bituminous coal (activation time: 2 hr) | 6 | 1.33 | 1.75 | 0.99 | 0.54 | 0.960 | 0.874 | 34.2 |
| Com. Ex. 12 | Soft coal (activation time: 2 hr) | 3 | 1.95 | 1.54 | 0.64 | 0.33 | 0.321 | 0.982 | 33.5 |
| Com. Ex. 13 | KURARAY COAL KW | 3 | 1.29 | 0.80 | 0.48 | 0.59 | 0.092 | 0.591 | 30.2 |
| Com. Ex. 14 | KURARAY COAL GC | 1 | 2.03 | 1.11 | 0.28 | 0.44 | 0.378 | 0.544 | 53.1 |
| Com. Ex. 15 | KURARAY COAL GLC | 1 | 4.94 | 0.57 | 0.21 | 0.67 | 0.303 | 0.176 | 62.3 |
| Com. Ex. 16 | Com. Ex. 5 treated at 930° C. | 9 | 2.76 | 3.21 | 0.19 | 0.22 | 0.177 | 0.297 | 7.2 |

TABLE 1-continued

| Sample No. | Raw material | Number of repetitions of catalyst (times) | Oxygen content (%) | Nitrogen content (%) | Sulfur content (%) | Hydrogen content (%) | Amount of acidic surface functional group (meq/g) | Amount of basic surface functional group (meq/g) | Benzene adsorption capacity (%) |
|---|---|---|---|---|---|---|---|---|---|
| Ex. 1 | Bituminous coal (activation time: 5 hr) | 15 | 2.80 | 1.10 | 0.71 | 0.64 | 0.142 | 0.647 | 36.1 |
| Ex. 2 | Anthracite coal (activation time: 5 hr) | 14 | 1.43 | 0.92 | 0.53 | 0.41 | 0.236 | 0.660 | 37.5 |
| Ex. 3 | Wood charcoal (activation time: 5 hr) | 13 | 4.24 | 2.28 | 1.17 | 0.51 | 0.179 | 0.731 | 39.6 |
| Ex. 4 | Bituminous coal (activation time: 20 hr) | 13 | 2.71 | 1.15 | 0.69 | 0.62 | 0.133 | 0.652 | 35.1 |
| Ex. 5 | Bituminous coal (activation time: 10 hr) | 14 | 2.65 | 1.11 | 0.82 | 0.59 | 0.127 | 0.661 | 36.7 |
| Ex. 6 | Bituminous coal (activation time: 18 hr) | 15 | 2.39 | 1.18 | 0.88 | 0.58 | 0.119 | 0.597 | 38.4 |

As apparent from Table 1, according to each of the activated carbons obtained in Comparative Examples 1 to 16, at least one content among the oxygen content (O), the nitrogen content (N), the sulfur content (S), and the hydrogen content (H) is excessively higher or lower than the given contents, and the number of repetitive use as a catalyst is 1 to 9. This means that the repetitive use of the activated carbon significantly lowers the catalytic activity thereof.

In contrast, according to each of Example 1 to 6, the oxygen content (O), the nitrogen content (N), the sulfur content (S), the hydrogen content (H) are within the given concentration ranges, and the number of repetitive use as a catalyst is 13 to 15, which is significantly improved. It is clear that the activated carbon maintains a high catalytic activity to allow the repetitive use.

Comparative Example 17

As Comparative Example 17, activated carbon SA-1 manufactured by NORIT described in Patent Document 3 was used and evaluated. The activated carbon proved to have the oxygen content and the sulfur content, each being beyond given ranges, and to have the number of repetitive use as a catalyst being 7.

Comparative Example 18

Bituminous coal as a carbonaceous raw material was subjected to the above-mentioned carbonization treatment, and the resulting carbonized product was placed in a furnace. A mixed gas having a water vapor partial pressure of 3%, a carbon dioxide partial pressure of 3%, and a nitrogen partial pressure of 94% was introduced into the furnace at a flow rate of 50 L/minute relative to 500 g of the resulting carbonized product, and the carbonized product was treated at an activation temperature of 900° C. for an activation time of 60 hours to produce an activated carbon of Comparative Example 18. The resulting activated carbon proved to have the oxygen content being beyond a given range and to have the number of repetitive use as a catalyst being 3.

Comparative Example 19

Wood charcoal as a carbonaceous raw material was subjected to the above-mentioned carbonization treatment, and the resulting carbonized product was placed in a furnace. A mixed gas having a water vapor partial pressure of 50%, a carbon dioxide partial pressure of 30%, and a nitrogen partial pressure of 20% was introduced into the furnace at a flow rate of 50 L/minute relative to 500 g of the resulting carbonized product, and the carbonized product was treated at an activation temperature of 900° C. for an activation time of 2 hours to produce an activated carbon of Comparative Example 19. The resulting activated carbon proved to have the oxygen content being beyond a given range and to have the number of repetitive use as a catalyst being 5.

Comparative Example 20

Anthracite coal as a carbonaceous raw material was subjected to the above-mentioned carbonization treatment, and the resulting carbonized product was placed in a furnace. A mixed gas having a water vapor partial pressure of 50%, a carbon dioxide partial pressure of 30%, and a nitrogen partial pressure of 20% was introduced into the furnace at a flow rate of 50 L/minute relative to 500 g of the resulting carbonized product, and the carbonized product was treated at an activation temperature of 900° C. for an activation time of 2 hours to produce an activated carbon of Comparative Example 20. The resulting activated carbon proved to have the nitrogen content being beyond a given range and to have the number of repetitive use as a catalyst being 2.

Comparative Example 21

To 100 g of the activated carbon of Comparative Example 4 was added 1 L of 1-N nitric acid, and the resultant was boiled for one hour and then washed with water to produce an activated carbon of Comparative Example 21. The resulting activated carbon proved to have the nitrogen content being beyond a given range and to have the number of repetitive use as a catalyst being 5.

Comparative Example 22

Anthracite coal as a carbonaceous raw material was subjected to the above-mentioned carbonization treatment, and the resulting carbonized product was placed in a furnace. A mixed gas having a water vapor partial pressure of 30%, a carbon dioxide partial pressure of 30%, and a nitrogen partial pressure of 40% was introduced into the furnace at a flow rate of 40 L/minute relative to 500 g of the resulting carbonized product, and the carbonized product was treated at an activation temperature of 900° C. for an activation time of 2 hours to produce an activated carbon of Comparative Example 22. The resulting activated carbon proved to have the sulfur content being beyond a given range and to have the number of repetitive use as a catalyst being 4.

Comparative Example 23

Petroleum coke as a carbonaceous raw material was subjected to the above-mentioned carbonization treatment, and the resulting carbonized product was placed in a furnace. A mixed gas having a water vapor partial pressure of 5%, a carbon dioxide partial pressure of 5%, and a nitrogen partial pressure of 90% was introduced into the furnace at a flow rate of 30 L/minute relative to 500 g of the resulting carbonized product, and the carbonized product was treated at an activation temperature of 900° C. for an activation time of 3 hours to produce an activated carbon of Comparative Example 23. The resulting activated carbon proved to have the sulfur content being beyond a given range and to have the number of repetitive use as a catalyst being 3.

Comparative Example 24

Coconut shell as a carbonaceous raw material was subjected to the above-mentioned carbonization treatment, and the resulting carbonized product was placed in a furnace. A mixed gas having a water vapor partial pressure of 5%, a carbon dioxide partial pressure of 5%, and a nitrogen partial pressure of 90% was introduced into the furnace at a flow rate of 30 L/minute relative to 500 g of the resulting carbonized product, and the carbonized product was treated at an activation temperature of 900° C. for an activation time of 60 hours to produce an activated carbon of Comparative Example 24. The resulting activated carbon proved to have the hydrogen content being beyond a given range and to have the number of repetitive use as a catalyst being 2.

Comparative Example 25

Wood charcoal as a carbonaceous raw material was subjected to the above-mentioned carbonization treatment, and the resulting carbonized product was placed in a furnace. A mixed gas having a water vapor partial pressure of 40%, a carbon dioxide partial pressure of 5%, and a nitrogen partial pressure of 55% was introduced into the furnace at a flow rate of 20 L/minute relative to 500 g of the resulting carbonized product, and the carbonized product was treated at an activation temperature of 900° C. for an activation time of 3 hours to produce an activated carbon of Comparative Example 25. The resulting activated carbon proved to have the hydrogen content being beyond a given range and to have the number of repetitive use as a catalyst being 6.

Example 7

Wood charcoal as a carbonaceous raw material was subjected to the above-mentioned carbonization treatment, and the resulting carbonized product was placed in a furnace. A mixed gas having a water vapor partial pressure of 30%, a carbon dioxide partial pressure of 30%, and a nitrogen partial pressure of 40% was introduced into the furnace at a flow rate of 40 L/minute relative to 500 g of the resulting carbonized product, and the carbonized product was treated at an activation temperature of 850° C. for an activation time of 3 hours to produce an activated carbon of Example 7. The resulting activated carbon proved to have all values of the physical properties being within given ranges and to have the number of repetitive use as a catalyst being 12.

Example 8

Wood charcoal as a carbonaceous raw material was subjected to the above-mentioned carbonization treatment, and the resulting carbonized product was placed in a furnace. A mixed gas having a water vapor partial pressure of 20%, a carbon dioxide partial pressure of 40%, and a nitrogen partial pressure of 40% was introduced into the furnace at a flow rate of 10 L/minute relative to 500 g of the resulting carbonized product, and the carbonized product was treated at an activation temperature of 900° C. for an activation time of 7 hours to produce an activated carbon of Example 8. The resulting activated carbon proved to have all values of the physical properties being within given ranges and to have the number of repetitive use as a catalyst being 13.

Example 9

Anthracite coal as a carbonaceous raw material was subjected to the above-mentioned carbonization treatment, and the resulting carbonized product was placed in a furnace. A mixed gas having a water vapor partial pressure of 30%, a carbon dioxide partial pressure of 30%, and a nitrogen partial pressure of 40% was introduced into the furnace at a flow rate of 10 L/minute relative to 500 g of the resulting carbonized product, and the carbonized product was treated at an activation temperature of 900° C. for an activation time of 9 hours to produce an activated carbon of Example 9. The resulting activated carbon proved to have all values of the physical properties being within given ranges and to have the number of repetitive use as a catalyst being 13.

Example 10

Wood charcoal as a carbonaceous raw material was subjected to the above-mentioned carbonization treatment, and the resulting carbonized product was placed in a furnace. A mixed gas having a water vapor partial pressure of 30%, a carbon dioxide partial pressure of 30%, and a nitrogen partial pressure of 40% was introduced into the furnace at a flow rate of 10 L/minute relative to 600 g of the resulting carbonized product, and the carbonized product was treated at an activation temperature of 900° C. for an activation time of 3 hours to produce an activated carbon of Example 10. The resulting activated carbon proved to have all values of the physical properties being within given ranges and to have the number of repetitive use as a catalyst being 15.

Example 11

Bituminous coal as a carbonaceous raw material was subjected to the above-mentioned carbonization treatment, and the resulting carbonized product was placed in a furnace. A mixed gas having a water vapor partial pressure of 30%, a carbon dioxide partial pressure of 30%, and a nitrogen partial pressure of 40% was introduced into the furnace at a flow rate of 10 L/minute relative to 500 g of the resulting carbonized product, and the carbonized product was treated at an activation temperature of 950° C. for an activation time of 3 hours to produce an activated carbon of Example 11. The resulting activated carbon proved to have all values of the physical properties being within given ranges and to have the number of repetitive use as a catalyst being 14.

Example 12

Wood charcoal as a carbonaceous raw material was subjected to the above-mentioned carbonization treatment, and the resulting carbonized product was placed in a furnace. A mixed gas having a water vapor partial pressure of 10%, a carbon dioxide partial pressure of 20%, and a nitrogen partial pressure of 70% was introduced into the furnace at a flow rate of 10 L/minute relative to 500 g of the resulting carbonized product, and the carbonized product was treated at an activation temperature of 900° C. for an activation time of 5 hours to produce an activated carbon of Example 12. The resulting activated carbon proved to have all values of the physical properties being within given ranges and to have the number of repetitive use as a catalyst being 12.

Example 13

Anthracite coal as a carbonaceous raw material was subjected to the above-mentioned carbonization treatment, and the resulting carbonized product was placed in a furnace. A mixed gas having a water vapor partial pressure of 30%, a carbon dioxide partial pressure of 30%, and a nitrogen partial pressure of 40% was introduced into the furnace at a flow rate of 40 L/minute relative to 500 g of the resulting carbonized product, and the carbonized product was treated at an activation temperature of 900° C. for an activation time of 7 hours to produce an activated carbon of Example 13. The resulting activated carbon proved to have all values of the physical properties being within given ranges and to have the number of repetitive use as a catalyst being 11.

The evaluation of the activated carbons obtained in Examples 7 to 13 and Comparative Examples 17 to 25 are shown in Table 2.

TABLE 2

| Sample No. | Raw material | Number of repetitions of catalyst (times) | Oxygen content (%) | Nitrogen content (%) | Sulfur content (%) | Hydrogen content (%) | Amount of acidic surface functional group (meq/g) | Amount of basic surface functional group (meq/g) | Benzene adsorption capacity (%) |
|---|---|---|---|---|---|---|---|---|---|
| Com. Ex. 17 | SA-1 manufactured by Norit | 7 | 4.38 | 1.20 | 2.14 | 0.56 | 0.226 | 1.233 | 33.2 |
| Com. Ex. 18 | Bituminous coal | 3 | 1.20 | 0.94 | 0.52 | 0.60 | 0.090 | 0.631 | 25.4 |
| Com. Ex. 19 | Wood charcoal | 5 | 4.50 | 1.52 | 0.77 | 0.55 | 0.678 | 0.298 | 30.1 |
| Com. Ex. 20 | Anthracite coal | 2 | 2.01 | 0.80 | 0.54 | 0.55 | 0.103 | 1.023 | 33.8 |
| Com. Ex. 21 | Com. Ex. 4 treated with 1-N nitric acid | 5 | 3.23 | 2.40 | 0.91 | 0.62 | 0.333 | 0.586 | 32.5 |
| Com. Ex. 22 | Anthracite coal | 4 | 2.11 | 0.98 | 0.40 | 0.61 | 0.118 | 1.101 | 36.1 |
| Com. Ex. 23 | Petroleum coke | 3 | 1.66 | 2.03 | 1.30 | 0.45 | 0.224 | 0.166 | 25.8 |
| Com. Ex. 24 | Coconut shell | 2 | 2.56 | 1.54 | 0.51 | 0.30 | 0.098 | 0.871 | 24.2 |
| Com. Ex. 25 | Wood charcoal | 6 | 2.49 | 0.99 | 0.67 | 0.70 | 0.661 | 0.301 | 40.4 |
| Ex. 7 | Wood charcoal | 12 | 1.50 | 2.20 | 1.15 | 0.58 | 0.231 | 0.644 | 27.2 |
| Ex. 8 | Wood charcoal | 13 | 4.20 | 2.23 | 1.10 | 0.52 | 0.249 | 0.703 | 45.1 |
| Ex. 9 | Anthracite coal | 13 | 1.45 | 1.00 | 0.67 | 0.51 | 0.242 | 0.636 | 40.1 |
| Ex. 10 | Wood charcoal | 15 | 3.13 | 2.20 | 0.81 | 0.58 | 0.256 | 0.722 | 35.1 |
| Ex. 11 | Bituminous coal | 14 | 2.11 | 1.13 | 0.60 | 0.60 | 0.125 | 0.674 | 35.6 |
| Ex. 12 | Wood charcoal | 12 | 3.88 | 2.14 | 1.10 | 0.50 | 0.237 | 0.614 | 31.1 |
| Ex. 13 | Anthracite coal | 11 | 1.58 | 0.92 | 0.66 | 0.45 | 0.255 | 0.652 | 39.3 |

As apparent from Table 2, according to each of the activated carbons obtained in Comparative Examples 17 to 25, at least one content among the oxygen content (O), the nitrogen content (N), the sulfur content (S), and the hydrogen content (H) is excessively higher or lower than the given contents, and the number of repetitive use as a catalyst is 2 to 7. This means that the repetitive use of the activated carbon significantly lowers the catalytic activity thereof.

In contrast, according to each of Example 7 to 13, the oxygen content (O), the nitrogen content (N), the sulfur content (S), the hydrogen content (H) are within the given concentration ranges, and the number of repetitive use as a catalyst is 11 to 15, which is significantly improved. It is clear that the activated carbon maintains a high catalytic activity to allow the repetitive use.

Each catalyst activated carbon obtained in Comparative Examples and Examples was tested according to the above-mentioned [Process for producing N-(phosphonomethyl)glycine] and was evaluated for the function or activity as a catalyst. Tables 3 to 6 show the yield and the purity (the change of the yield and the purity depending on the number of repetitions) in each catalyst activated carbon.

TABLE 3

| Sample No. | Raw material | Number of repetitions of catalyst (times) | Yield (%) | Purity (%) |
|---|---|---|---|---|
| Com. Ex. 1 | Anthracite coal (activation time: 1 hr) | 1 | 54.1 | 72.3 |
| Com. Ex. 2 | Soft coal (activation time: 1 hr) | 1 | 55.9 | 64.9 |
| Com. Ex. 3 | Bituminous coal (activation time: 1 hr) | 1 | 89.1 | 97.2 |
| | | 3 | 90.4 | 97.4 |
| | | 5 | 77.1 | 66.6 |
| Com. Ex. 4 | Petroleum coke (activation time: 1 hr) | 1 | 89.1 | 97.9 |
| | | 3 | 90.8 | 98.4 |
| | | 5 | 92.1 | 98.1 |
| | | 7 | 77.2 | 74.5 |
| Com. Ex. 5 | PAN (activation time: 1 hr) | 1 | 90.1 | 98.3 |
| | | 5 | 92.3 | 97.6 |
| | | 9 | 90.8 | 98.8 |
| | | 12 | 71.5 | 70.5 |
| Com. Ex. 6 | Coconut shell activated carbon (activation time: 1 hr) | 1 | 43.2 | 61.9 |
| Com. Ex. 7 | Wood charcoal (activation time: 1 hr) | 1 | 89.8 | 98.6 |
| | | 3 | 90.1 | 98.8 |
| | | 5 | 60.2 | 72.3 |
| Com. Ex. 8 | Com. Ex. 2 treated with 6-N nitric acid | 1 | 44.4 | 54.6 |
| Com. Ex. 9 | Com. Ex. 8 treated at 930° C. | 1 | 90.6 | 98.1 |
| | | 3 | 92.6 | 97.9 |
| | | 5 | 71.3 | 97.5 |
| Com. Ex. 10 | Com. Ex. 4 treated with 6-N nitric acid | 1 | 32.1 | 44.4 |
| Com. Ex. 11 | Bituminous coal (activation time: 2 hr) | 1 | 90.2 | 98.8 |
| | | 3 | 89.8 | 97.9 |
| | | 5 | 92.7 | 98.4 |
| | | 7 | 75.2 | 69.6 |
| Com. Ex. 12 | Soft coal (activation time: 2 hr) | 1 | 88.5 | 98.2 |
| | | 3 | 90.6 | 97.4 |
| | | 5 | 58.2 | 62.9 |
| Com. Ex. 13 | KURARAY COAL KW | 1 | 88.3 | 96.5 |
| | | 3 | 85.2 | 97.1 |
| | | 5 | 75.8 | 68.9 |
| Com. Ex. 14 | KURARAY COAL GC | 1 | 55.8 | 76.1 |
| Com. Ex. 15 | KURARAY COAL GLC | 1 | 55.5 | 68.4 |
| Com. Ex. 16 | Com. Ex. 5 treated at 930° C. | 1 | 91.6 | 95.8 |
| | | 5 | 93.4 | 96.2 |
| | | 9 | 91.2 | 94.8 |
| | | 12 | 78.2 | 89.1 |

TABLE 4

| Sample No. | Raw material | Number of repetitions of catalyst (times) | Yield (%) | Purity (%) |
|---|---|---|---|---|
| Ex. 1 | Bituminous coal (activation time: 5 hr) | 1 | 90.9 | 98.6 |
| | | 5 | 92.3 | 97.3 |
| | | 10 | 97.8 | 98.1 |
| | | 15 | 95.5 | 97.9 |
| | | 20 | 93.3 | 98.1 |
| Ex. 2 | Anthracite coal (activation time: 5 hr) | 1 | 90.1 | 98.3 |
| | | 5 | 93.4 | 97.4 |
| | | 10 | 95.8 | 98.4 |
| | | 15 | 80.1 | 98.1 |
| Ex. 3 | Wood charcoal (activation time: 5 hr) | 1 | 91.4 | 98.1 |
| | | 5 | 90.2 | 97.5 |
| | | 10 | 94.4 | 98.9 |
| | | 15 | 82.7 | 94.3 |
| Ex. 4 | Bituminous coal (activation time: 20 hr) | 1 | 91.9 | 98.5 |
| | | 5 | 92.5 | 98.9 |
| | | 10 | 97.2 | 95.3 |
| | | 15 | 97.9 | 94.5 |
| | | 20 | 90.1 | 92.1 |
| Ex. 5 | Bituminous coal (activation time: 10 hr) | 1 | 93.2 | 93.8 |
| | | 5 | 95.8 | 94.3 |
| | | 10 | 98.3 | 97.7 |
| | | 15 | 93.8 | 96.3 |
| | | 20 | 89.3 | 93.1 |
| Ex. 6 | Bituminous coal (activation time: 18 hr) | 1 | 95.5 | 95.4 |
| | | 5 | 98.2 | 97.1 |
| | | 10 | 93.5 | 98.1 |
| | | 15 | 94.9 | 94.4 |
| | | 20 | 92.2 | 92.2 |

TABLE 5

| Sample No. | Raw material | Number of repetitions of catalyst (times) | Yield (%) | Purity (%) |
|---|---|---|---|---|
| Com. Ex. 17 | SA-1 manufactured by Norit | 1 | 91.3 | 94.8 |
| | | 5 | 92.2 | 97.6 |
| | | 9 | 70.1 | 79.4 |
| Com. Ex. 18 | Bituminous coal | 1 | 90.4 | 96.5 |
| | | 3 | 93.3 | 95.2 |
| | | 5 | 73.2 | 90.1 |
| Com. Ex. 19 | Wood charcoal | 1 | 83.2 | 94.4 |
| | | 3 | 74.1 | 80.7 |
| Com. Ex. 20 | Anthracite coal | 1 | 93.1 | 94.9 |
| | | 3 | 68.3 | 81.1 |
| Com. Ex. 21 | Com. Ex. 4 treated with 1-N nitric acid | 1 | 89.3 | 93.4 |
| | | 5 | 93.7 | 94.4 |
| | | 7 | 76.2 | 85.4 |
| Com. Ex. 22 | Anthracite coal | 1 | 78.3 | 88.5 |
| Com. Ex. 23 | Petroleum coke | 1 | 88.9 | 94.8 |
| | | 3 | 90.5 | 93.5 |
| | | 5 | 71.8 | 88.9 |
| Com. Ex. 24 | Coconut shell | 1 | 45.6 | 66.1 |
| Com. Ex. 25 | Wood charcoal | 1 | 91.1 | 94.9 |
| | | 3 | 89.4 | 94.6 |
| | | 5 | 79.4 | 90.4 |

TABLE 6

| Sample No. | Raw material | Number of repetitions of catalyst (times) | Yield (%) | Purity (%) |
|---|---|---|---|---|
| Ex. 7 | Wood charcoal | 1 | 89.4 | 94.7 |
| | | 5 | 93.2 | 95.1 |
| | | 10 | 90.7 | 97.4 |
| | | 15 | 89.4 | 93.1 |
| | | 20 | 82.3 | 94.4 |

TABLE 6-continued

| Sample No. | Raw material | Number of repetitions of catalyst (times) | Yield (%) | Purity (%) |
|---|---|---|---|---|
| Ex. 8 | Wood charcoal | 1 | 90.9 | 93.3 |
|  |  | 5 | 92.3 | 94.5 |
|  |  | 10 | 94.5 | 93.5 |
|  |  | 15 | 98.9 | 97.4 |
|  |  | 20 | 83.1 | 94.0 |
| Ex. 9 | Anthracite coal | 1 | 83.3 | 98.4 |
|  |  | 5 | 87.4 | 97.4 |
|  |  | 10 | 93.8 | 94.4 |
|  |  | 15 | 90.4 | 93.8 |
|  |  | 20 | 80.8 | 94.4 |
| Ex. 10 | Wood charcoal | 1 | 91.1 | 98.5 |
|  |  | 5 | 92.8 | 98.7 |
|  |  | 10 | 90.9 | 96.8 |
|  |  | 15 | 89.4 | 97.1 |
|  |  | 20 | 82.1 | 93.3 |
| Ex. 11 | Bituminous coal | 1 | 95.8 | 98.7 |
|  |  | 5 | 96.4 | 99.1 |
|  |  | 10 | 94.1 | 96.3 |
|  |  | 15 | 93.8 | 97.7 |
|  |  | 20 | 95.3 | 98.1 |
| Ex. 12 | Wood charcoal | 1 | 90.8 | 93.7 |
|  |  | 5 | 90.4 | 95.1 |
|  |  | 10 | 94.6 | 94.4 |
|  |  | 15 | 92.7 | 93.7 |
|  |  | 20 | 88.8 | 94.0 |
| Ex. 13 | Anthracite coal | 1 | 80.5 | 94.9 |
|  |  | 5 | 83.4 | 97.9 |
|  |  | 10 | 86.9 | 96.1 |
|  |  | 15 | 90.8 | 95.4 |
|  |  | 20 | 84.8 | 94.4 |

In Comparative Examples, the decomposition of hydrogen peroxide depends on the number of repetitive use of the activated carbon. In the production reaction of N-(phosphonomethyl)glycine, the initial yield or purity is satisfied, however the repetitive use of the activated carbon for the reaction causes the lowering of the function or activities as a catalyst. The decrease of the yield and purity of the N-(phosphonomethyl)glycine is probably caused by deteriorating the decomposition rate of hydrogen peroxide.

In Examples, it is confirmed that the elementary composition is within the range defined in the present invention and the production reaction of N-(phosphonomethyl)glycine maintains a high yield and purity even if the number of repetitive use of the activated carbon is increased. This shows that the elementary composition defined in the present invention is successful for not only the decomposition reaction of hydrogen peroxide but also the production reaction of N-(phosphonomethyl)glycine.

The present invention has been described with reference to preferred embodiments thereof. According to the present invention, use of the activated carbon of the present invention in the presence of both water and hydrogen peroxide produces N-(phosphonomethyl)glycine efficiently from N-(phosphonomethyl)iminodiacetic acid.

[Decomposition of Chloramine]

Using each activated carbon obtained in Comparative Examples and Examples, the decomposition amount of chloramine was measured as follows.

The activated carbon was added to 100 mL of a chloramine (monochloroamine) aqueous solution in which the chloramine concentration had been adjusted to about 100 ppm, and the mixture was shaken at 25° C. for 2 hours. Thereafter, the mixture was filtered through a filter paper, and the residual chloramine concentration in the filtrate was measured by the following DPD absorption photometry. From the relationship between the chloramine concentration and the free residual chlorine, the decomposition amount of chloramine (mg/g-activated carbon) at a residual concentration of 3 ppm was determined.

[Method for Quantitatively Determining Chloramine: DPD Absorption Photometry]

(1) Measurement of Free Residual Chlorine

A phosphoric acid buffer (2.5 mL) is taken in a 50-mL colorimetric tube with ground stopper, and 0.5 g of N,N-diethyl-p-phenylenediamine (DPD) reagent is added to the buffer. The above-mentioned filtrate is then added thereto to adjust the total amount to 50 mL. After mixing, an appropriate amount of the colored sample solution is taken in an absorption cell, and the absorbency is measured around a wavelength of 510 to 555 nm by a photoelectric spectrophotometer. The free residual chlorine (mg/L) in 1 L of the sample solution is determined based on the working curve (or analytical curve) made by the following (2).

(2) Preparation of Working Curve of Free Residual Chlorine

A standard chlorine water is prepared and is diluted with dilution water to prepare a series of standards having several levels. Immediately after the preparation, the absorbency of each standard series is measured in the same manner as in the above-mentioned (1) to determine the concentration (mg/L) of the free residual chlorine. On the basis of these absorbencies, a working curve is prepared.

(3) Measurement of Residual Chlorine in Each Standard Series

Potassium iodide (about 0.5 g) is added to the solution colored in the above-mentioned (1) and dissolved therein. After the solution is allowed to stand for about 2 minutes, the residual chlorine (mg/L) in the resulting sample is determined in the same manner as in the above-mentioned (1).

(4) Measurement of Bonded Residual Chlorine (Chloramine)

The difference between the above-mentioned residual chlorine and the free residual chlorine is regarded as a concentration (mg/L) of a bonded residual chlorine (chloramine).

The results are shown in Table 7.

TABLE 7

| Activated carbon | Amount of chloramine decomposition at residual concentration of 3 ppm (mg/g-activated carbon) |
|---|---|
| Com. Ex. 6 | 8 |
| Com. Ex. 3 | 20 |
| Ex. 1 | 130 |
| Ex. 4 | 150 |

From Table 7, the activated carbons of Examples decompose chloramine in extremely high quantities compared with the activated carbons of Comparative Examples.

INDUSTRIAL APPLICABILITY

The activated carbon of the present invention is useful as an oxidation catalyst or a decomposition catalyst for a peroxide (e.g., hydrogen peroxide), a sulfide, sulfur dioxide, a nitrogen oxide, and other substrates and is also useful as a decomposition catalyst for a chloramine. Moreover, the activated carbon catalyst of the present invention catalyzes an oxidation reaction, and the activated carbon catalyst in the presence of both water and hydrogen peroxide allows N-(phosphonomethyl)glycine to be efficiently produced from N-(phosphonomethyl)iminodiacetic acid. Further, due to the maintenance of high catalytic activity, the activated carbon is highly recyclable and reduces an activated carbon waste, and can result in cost saving. Thus the activated carbon is useful as an activated carbon catalyst for many oxidation reactions.

The invention claimed is:

1. An activated carbon, comprising, based on a total mass of the activated carbon:
   (a) from 1.40 to 4.30% by mass of oxygen;
   (b) from 0.90 to 2.30% by mass of nitrogen;
   (c) from 0.50 to 1.20% by mass of sulfur; and
   (d) from 0.40 to 0.65% by mass of hydrogen.

2. A decomposition catalyst, comprising an activated carbon comprising, based on a total mass of the activated carbon:
   (a) from 1.40 to 4.30% by mass of oxygen;
   (b) from 0.90 to 2.30% by mass of nitrogen;
   (c) from 0.50 to 1.20% by mass of sulfur; and
   (d) from 0.40 to 0.65% by mass of hydrogen.

3. The decomposition catalyst of claim 2, wherein the activated carbon comprises, based on a total mass of the activated carbon:
   (a) from 1.40 to 3.5% by mass of oxygen;
   (b) from 0.90 to 2.0% by mass of nitrogen;
   (c) from 0.50 to 1.00% by mass of sulfur; and
   (d) from 0.40 to 0.65% by mass of hydrogen.

4. The decomposition catalyst of claim 2, wherein the activated carbon comprises, based on a total mass of the activated carbon:
   (a) from 1.40 to 3.0% by mass of oxygen;
   (b) from 0.90 to 1.75% by mass of nitrogen;
   (c) from 0.50 to 0.90% by mass of sulfur; and
   (d) from 0.40 to 0.65% by mass of hydrogen.

5. The decomposition catalyst of claim 2, satisfying at least one selected from the group consisting of:
   (e) further comprising an amount of an acidic surface functional group in a range from 0.10 to 0.36 meq/g;
   (f) further comprising an amount of a basic surface functional group in a range from 0.50 to 1.30 meq/g; and
   (g) having a benzene adsorption capacity in a range from 25 to 50%.

6. The decomposition catalyst of claim 2, satisfying at least one selected from the group consisting of:
   (e) comprising an amount of an acidic surface functional group in a range from 0.10 to 0.30 meq/g;
   (f) comprising an amount of a basic surface functional group in a range from 0.50 to 1.00 meq/g; and
   (g) having a benzene adsorption capacity in a range from 25 to 47%.

7. The decomposition catalyst of claim 2, further comprising (e) an amount of an acidic surface functional group in a range from 0.10 to 0.36 meq/g.

8. The decomposition catalyst of claim 2, further comprising (f) an amount of a basic surface functional group in a range from 0.50 to 1.30 meq/g.

9. The decomposition catalyst of claim 2, having (g) a benzene adsorption capacity in a range from 25 to 50%.

10. The decomposition catalyst of claim 2, further comprising (e) an amount of an acidic surface functional group in a range from 0.10 to 0.30 meq/g.

11. The decomposition catalyst of claim 2, further comprising (f) an amount of a basic surface functional group in a range from 0.50 to 1.00 meq/g.

12. The decomposition catalyst of claim 2, having (g) a benzene adsorption capacity in a range from 25 to 47%.

13. A process for producing N-(phosphonomethyl)glycine, the process comprising:
    oxidizing N-(phosphonomethyl)iminodiacetic acid with an oxidizing agent in the presence of an activated carbon,
    wherein the activated carbon comprises, based on a total mass of the activated carbon:
    (a) from 1.40 to 4.30% by mass of oxygen;
    (b) from 0.90 to 2.30% by mass of nitrogen;
    (c) from 0.50 to 1.20% by mass of sulfur; and
    (d) from 0.40 to 0.65% by mass of hydrogen, and
    wherein the oxidizing agent comprises a peroxide.

14. The process of claim 13, wherein the amount of the activated carbon is 0.5 to 300 parts by weight, relative to 100 parts by weight of the N-(phosphonomethyl)iminodiacetic acid.

15. The process of claim 13, wherein the amount of the peroxide is 10 to 100 parts by weight, relative to 100 parts by weight of the N-(phosphonomethyl)iminodiacetic acid.

16. The process of claim 13, wherein the peroxide is hydrogen peroxide.

17. The process of claim 16, wherein a decomposition rate of hydrogen peroxide is not less than 1,000 mg-$H_2O_2$/g-activated carbon/hr.

18. A process for removing a peroxide or a chloramine, the process comprising:
    contacting a peroxide or a chloramine with an activated carbon comprising, based on a total mass of the activated carbon
    (a) from 1.40 to 4.30% by mass of oxygen;
    (b) from 0.90 to 2.30% by mass of nitrogen;
    (c) from 0.50 to 1.20% by mass of sulfur; and
    (d) from 0.40 to 0.65% by mass of hydrogen.

* * * * *